United States Patent
Muller et al.

(10) Patent No.: US 9,657,072 B2
(45) Date of Patent: May 23, 2017

(54) MODIFIED PEPTIDES AND THEIR USE FOR TREATING AUTOIMMUNE DISEASES

(71) Applicants: Centre National De La Rechereche Scientifique, Paris (FR); Immupharma France SA, Mulhouse (FR)

(72) Inventors: Sylviane Muller, Strasbourg (FR); Jean-Paul Briand, Strasbourg (FR); Robert H. Zimmer, Mulhouse (FR)

(73) Assignees: Centre National De La Recherche Scientifique, Paris (FR); Immupharma France SA, Mulhouse (FR)

( * ) Notice: Subject to any disclaimer, the term of this patent is extended or adjusted under 35 U.S.C. 154(b) by 89 days.

(21) Appl. No.: 14/562,350

(22) Filed: Dec. 5, 2014

(65) Prior Publication Data

US 2015/0111835 A1  Apr. 23, 2015

Related U.S. Application Data

(63) Continuation of application No. PCT/IB2011/003256, filed on Dec. 13, 2011.

(51) Int. Cl.
*C07K 14/47* (2006.01)
*C07K 7/08* (2006.01)
*A61K 38/17* (2006.01)
*A61K 38/00* (2006.01)

(52) U.S. Cl.
CPC .......... *C07K 14/47* (2013.01); *A61K 38/1709* (2013.01); *C07K 7/08* (2013.01); *A61K 38/00* (2013.01)

(58) Field of Classification Search
CPC .................................................. C07K 14/47
See application file for complete search history.

(56) References Cited

U.S. PATENT DOCUMENTS

| | | | |
|---|---|---|---|
| 4,522,811 A | 6/1985 | Eppstein | |
| 7,872,098 B1 * | 1/2011 | Muller | C07K 14/47 530/326 |
| 2003/0186849 A1 * | 10/2003 | Zimmer | A61K 38/02 424/185.1 |

FOREIGN PATENT DOCUMENTS

| | | |
|---|---|---|
| JP | 2005-512958 | 5/2012 |
| RU | 2214417 C2 | 10/2003 |
| WO | WO 03/020747 | 3/2003 |
| WO | WO 03/025014 | 3/2003 |

OTHER PUBLICATIONS

Vogt, 1995, Oxidation of Methionyl Residues in Proteins: Tools, Targets, and Reversal, Free Radical Biology & Medicine, 18(1): 93-105.*
Cui et al., epub Dec. 7, 2011, Modulating protein activity and cellular function by methionine residue oxidation, Amino Acids, 43: 505-517.*
International Search Report, issued Jun. 4, 2012, for PCT/IB2011/003256, filed Dec. 13, 2011.
Written Opinion of the International Searching Authority, issued Jun. 4, 2012, for PCT/IB2011/003256, filed Dec. 13, 2011.
Arbuckle et al. N. Engl. J. Med. 349(16): 1526-1533 (2003).
Cambridge et al., Ann Rheum Dis 67: 1011-16 (2008).
D'Cruz et al., Lancet (2007), 369: 587-596.
Ho, Kim Yun et al.: "Comparing the effect on protein stability of methionine oxidation versus mutagenesis: Steps toward engineering oxidative resistance in proteins", protein engineering, oxford university press, surrey, GB, vol. 14, No. 5, May 1, 2001, pp. 343-347.
Holman, Ann NY Acad. Sci. 124(2): 800-6 (1965).
Kattah, Nichole Hanick, "Tetramers reveal CD4+ T cells that are specific for UI-70 in systemic lupus erythematosus", Stanford University, Dept. of Immunology, doctoral dissertation, 2010.
Lerner et al., Proc Natl Acad Sci USA. 76(11) 5495-9 (1979).
Lerner et al., Science 211 (4480): 400-2 (1981).
Manning, Mark Cornell et al.: "Stability of Protein Pharmaceuticals: An Update", Pharmaceutical research, klumer academic publishers-plenum publishers, NL, vol. 27, No. 4, Feb. 9, 2010, pp. 544-575.
Monneaux et al., 2003. Eur. J. Immunol. 33: 287-296.
Muller, Sylviane et al.: "Spliceosomal peptide P140 for immunotherapy of systemic lupus erythematosus: Results of an Early Phase II Clinical Trial", Arthritis & Rheumatism, vol. 58, No. 12, Dec. 1, 2008. pp. 3873-3883.
Nath SK, et al., Curr. Opin. Immunol. 2004; 16(6): 794-800.
Neimark and Briand, 1993, Pept Res. Jul.-Aug. 1993;6(4):219-228.
Orlando, M., "Modification of proteins and low molecular weight substances with hydroxyethyl starch (HES)", Inauguraldissertation, Geisen, 2003, p. 166, line 15.
Page, Nicolas et al.: "The Spliceosomal Phosphopeptide P140 Controls the Lupus Disease by Interacting with the HSC70 Protein and via a Mechanism Medicated by [gamma] [delta] T cells", PLOS ONE, vol. 4, No. 4, Jan. 1, 2009, p. E5273.
Page et al. Ann. Rheum Dis 2011; 70: 837-843 doi: 10.1136/ard.2010.139832.
Page et al. Autophagy 7(5), 539-540, May 1, 2011.
Wakeland EK, et al., Immunity 2001; 15(3): 397-408.

* cited by examiner

*Primary Examiner* — Amber D Steele
(74) *Attorney, Agent, or Firm* — Bryan D. Zerhusen; Locke Lord LLP

(57) ABSTRACT

The present invention relates to a peptide, or a salt thereof, comprising or consisting of the amino acid sequence IHM-VYSKRSGKPRGYAFIEY, comprising one or more post-translational modifications.

11 Claims, 4 Drawing Sheets

SEQUENCE LISTING

<160> NUMBER OF SEQ ID NOS: 6

<210> SEQ ID NO 1
<211> LENGTH: 21
<212> TYPE: PRT
<213> ORGANISM: Artificial sequence
<220> FEATURE:
<223> OTHER INFORMATION: derived from U1 snRNP 70 kDa

<400> SEQUENCE: 1

Arg Ile His Met Val Tyr Ser Lys Arg Ser Gly Lys Pro Arg Gly Tyr
1               5                   10                  15

Ala Phe Ile Glu Tyr
            20

<210> SEQ ID NO 2
<211> LENGTH: 20
<212> TYPE: PRT
<213> ORGANISM: Artificial sequence
<220> FEATURE:
<223> OTHER INFORMATION: derived from U1 snRNP 70 kDa

<400> SEQUENCE: 2

Ile His Met Val Tyr Ser Lys Arg Ser Gly Lys Pro Arg Gly Tyr Ala
1               5                   10                  15

Phe Ile Glu Tyr
            20

<210> SEQ ID NO 3
<211> LENGTH: 437
<212> TYPE: PRT
<213> ORGANISM: Homo sapiens

<400> SEQUENCE: 3

Met Thr Gln Phe Leu Pro Pro Asn Leu Leu Ala Leu Phe Ala Pro Arg
1               5                   10                  15

Asp Pro Ile Pro Tyr Leu Pro Pro Leu Glu Lys Leu Pro His Glu Lys
            20                  25                  30

-continued

```
His His Asn Gln Pro Tyr Cys Gly Ile Ala Pro Tyr Ile Arg Glu Phe
         35                  40                  45

Glu Asp Pro Arg Asp Ala Pro Pro Thr Arg Ala Glu Thr Arg Glu
 50                  55                  60

Glu Arg Met Glu Arg Lys Arg Glu Lys Ile Glu Arg Arg Gln Gln
 65                  70                  75                  80

Glu Val Glu Thr Glu Leu Lys Met Trp Asp Pro His Asn Asp Pro Asn
                 85                  90                  95

Ala Gln Gly Asp Ala Phe Lys Thr Leu Phe Val Ala Arg Val Asn Tyr
                100                 105                 110

Asp Thr Thr Glu Ser Lys Leu Arg Arg Glu Phe Glu Val Tyr Gly Pro
                115                 120                 125

Ile Lys Arg Ile His Met Val Tyr Ser Lys Arg Ser Gly Lys Pro Arg
            130                 135                 140

Gly Tyr Ala Phe Ile Glu Tyr Glu His Glu Arg Asp Met His Ser Ala
145                 150                 155                 160

Tyr Lys His Ala Asp Gly Lys Lys Ile Asp Gly Arg Arg Val Leu Val
                165                 170                 175

Asp Val Glu Arg Gly Arg Thr Val Lys Gly Trp Arg Pro Arg Arg Leu
                180                 185                 190

Gly Gly Gly Leu Gly Gly Thr Arg Arg Gly Gly Ala Asp Val Asn Ile
            195                 200                 205

Arg His Ser Gly Arg Asp Asp Thr Ser Arg Tyr Asp Glu Arg Pro Gly
            210                 215                 220

Pro Ser Pro Leu Pro His Arg Asp Arg Asp Asp Arg Glu Arg Glu
225                 230                 235                 240

Arg Arg Glu Arg Ser Arg Glu Arg Asp Lys Arg Glu Arg Arg
                245                 250                 255

Ser Arg Ser Arg Asp Arg Arg Arg Ser Arg Ser Arg Asp Lys Glu
            260                 265                 270

Glu Arg Arg Arg Ser Arg Glu Arg Ser Lys Asp Lys Asp Arg Asp Arg
            275                 280                 285

Lys Arg Arg Ser Ser Arg Ser Arg Glu Arg Ala Arg Arg Glu Arg Glu
290                 295                 300

Arg Lys Glu Glu Leu Arg Gly Gly Gly Asp Met Ala Glu Pro Ser
305                 310                 315                 320

Glu Ala Gly Asp Ala Pro Pro Asp Asp Gly Pro Pro Gly Glu Leu Gly
                325                 330                 335

Pro Asp Gly Pro Asp Gly Pro Glu Glu Lys Gly Arg Asp Arg Asp Arg
                340                 345                 350

Glu Arg Arg Arg Ser His Arg Ser Glu Arg Glu Arg Arg Asp Arg
                355                 360                 365

Asp Arg Asp Arg Asp Arg Asp Arg Glu His Lys Arg Gly Glu Arg Gly
                370                 375                 380

Ser Glu Arg Gly Arg Asp Glu Ala Arg Gly Gly Gly Gly Gln Asp
385                 390                 395                 400

Asn Gly Leu Glu Gly Leu Gly Asn Asp Ser Arg Asp Met Tyr Met Glu
                405                 410                 415

Ser Glu Gly Gly Asp Gly Tyr Leu Ala Pro Glu Asn Gly Tyr Leu Met
                420                 425                 430

Glu Ala Ala Pro Glu
                435
```

```
<210> SEQ ID NO 4
<211> LENGTH: 21
<212> TYPE: PRT
<213> ORGANISM: Artificial sequence
<220> FEATURE:
<223> OTHER INFORMATION: derived from U1 snRNP 70 kDa
<220> FEATURE:
<221> NAME/KEY: MOD_RES
<222> LOCATION: (4)..(4)
<223> OTHER INFORMATION: OXIDATION
<220> FEATURE:
<221> NAME/KEY: MOD_RES
<222> LOCATION: (10)..(10)
<223> OTHER INFORMATION: PHOSPHORYLATION

<400> SEQUENCE: 4

Arg Ile His Met Val Tyr Ser Lys Arg Ser Gly Lys Pro Arg Gly Tyr
1               5                   10                  15

Ala Phe Ile Glu Tyr
            20

<210> SEQ ID NO 5
<211> LENGTH: 20
<212> TYPE: PRT
<213> ORGANISM: Artificial sequence
<220> FEATURE:
<223> OTHER INFORMATION: derived from U1 snRNP 70 kDa
<220> FEATURE:
<221> NAME/KEY: MOD_RES
<222> LOCATION: (3)..(3)
<223> OTHER INFORMATION: OXIDATION
<220> FEATURE:
<221> NAME/KEY: MOD_RES
<222> LOCATION: (9)..(9)
<223> OTHER INFORMATION: PHOSPHORYLATION

<400> SEQUENCE: 5

Ile His Met Val Tyr Ser Lys Arg Ser Gly Lys Pro Arg Gly Tyr Ala
1               5                   10                  15

Phe Ile Glu Tyr
            20

<210> SEQ ID NO 6
<211> LENGTH: 66
<212> TYPE: DNA
<213> ORGANISM: Artificial Sequence
<220> FEATURE:
<223> OTHER INFORMATION: derived from U1 snRNP 70 kDa
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: misc_feature
<222> LOCATION: (15)..(15)
<223> OTHER INFORMATION: n is a, c, g, or t
<220> FEATURE:
<221> NAME/KEY: misc_feature
<222> LOCATION: (21)..(21)
<223> OTHER INFORMATION: n is a, c, g, or t
<220> FEATURE:
<221> NAME/KEY: misc_feature
<222> LOCATION: (27)..(27)
<223> OTHER INFORMATION: n is a, c, g, or t
<220> FEATURE:
<221> NAME/KEY: misc_feature
<222> LOCATION: (30)..(30)
<223> OTHER INFORMATION: n is a, c, g, or t
<220> FEATURE:
<221> NAME/KEY: misc_feature
<222> LOCATION: (33)..(33)
<223> OTHER INFORMATION: n is a, c, g, or t
```

```
<220> FEATURE:
<221> NAME/KEY: misc_feature
<222> LOCATION: (39)..(39)
<223> OTHER INFORMATION: n is a, c, g, or t
<220> FEATURE:
<221> NAME/KEY: misc_feature
<222> LOCATION: (42)..(42)
<223> OTHER INFORMATION: n is a, c, g, or t
<220> FEATURE:
<221> NAME/KEY: misc_feature
<222> LOCATION: (45)..(45)
<223> OTHER INFORMATION: n is a, c, g, or t
<220> FEATURE:
<221> NAME/KEY: misc_feature
<222> LOCATION: (51)..(51)
<223> OTHER INFORMATION: n is a, c, g, or t

<400> SEQUENCE: 6
mgnathcaya tggtntayws naarmgnwsn ggnaarccnm gnggntaygc nttyathgar      60 taytrr                                                                66
```

MODIFIED PEPTIDES AND THEIR USE FOR TREATING AUTOIMMUNE DISEASES

FIELD OF THE INVENTION

The present invention relates to a modified peptide, and its use for treating autoimmune diseases.

INCORPORATION BY REFERENCE

In compliance with 37 C.F.R. §1.52(e)(5), a .txt version of the computer readable form of the sequence listing information is submitted herewith, file name: 34187470_1-P140 seq listing_ST25.txt; size 7 KB; using PatentIn, and is hereby incorporated by reference in its entirety.

CROSS-REFERENCE TO RELATED APPELLATIONS

This application claims priority to PCT/IB2011/003256 filed Dec. 13, 2011 entitled Modified Peptides and their use for treating autoimmune diseases, which is incorporated herein by reference in its entirety.

BACKGROUND

Autoimmune diseases arise from an overactive immune response of the immune system against substances and tissues normally present in a multicellular organism, i.e. the immune system attacks its own components. This may be restricted to certain organs or involve a particular tissue in different places. The treatment of autoimmune diseases is typically with immunosuppression—medication which decreases the whole immune response.

Lupus is an autoimmune disease that is estimated to affect nearly 1.4 million Americans, primarily women between the ages of 20-40. Lupus involves antibodies that attack connective tissue. The principal form of lupus is a systemic one (systemic lupus erythematosus; SLE). SLE is a chronic autoimmune disease with strong genetic as well as environmental components (See, e.g., Hochberg M C, Dubois' Lupus Erythematosus. 5th ed., Wallace D J, Hahn B H, eds. Baltimore: Williams and Wilkins (1997); Wakeland E K, et al., *Immunity* 2001; 15(3):397-408; Nath S K, et al., *Curr. Opin. Immunol.* 2004; 16(6):794-800; D'Cruz et al., *Lancet* (2007), 369:587-596). Various additional forms of lupus are known, including, but not limited to, cutaneous lupus erythematosus (CLE), lupus nephritis (LN), neuropsychiatric lupus (NPLE) and neonatal lupus.

Untreated lupus can be fatal as it progresses from attack of skin and joints to internal organs, including lung, heart, and kidneys (with renal disease being the primary concern), thus making early and accurate diagnosis of and/or assessment of risk of developing lupus particularly critical. Lupus mainly appears as a series of flare-ups, with intervening periods of little or no disease manifestation. Kidney damage, measured by the amount of protein in the urine (proteinuria), is one of the most acute areas of damage associated with pathogenicity in SLE, and accounts for at least 50% of the mortality and morbidity of the disease, without any treatment.

Clinically, SLE is a heterogeneous disorder characterized by high-affinity autoantibodies (autoAbs). AutoAbs play an important role in the pathogenesis of SLE, and the diverse clinical manifestations of the disease are due to the deposition of antibody-containing immune complexes in blood vessels leading to inflammation in the kidney, brain and skin. AutoAbs also have direct pathogenic effects contributing to hemolytic anemia and thrombocytopenia. SLE is associated with the production of antinuclear antibodies, circulating immune complexes, and defect of the complement system. SLE has an incidence of about 1 in 700 women between the ages of 20 and 60, in black population. SLE can affect any organ system and can cause severe tissue damage. Numerous autoAbs of differing specificity are present in SLE. SLE patients often produce autoAbs having anti-DNA, anti-Ro, and anti-platelet specificity and that are capable of initiating clinical features of the disease, such as glomerulonephritis, arthritis, serositis, complete heart block in newborns, and hematologic abnormalities. These autoAbs are also possibly related to central nervous system disturbances. Arbuckle et al. described the development of autoAbs before the clinical onset of SLE (Arbuckle et al. *N. Engl. J. Med.* 349(16): 1526-1533 (2003)).

AutoAbs recognizing RNA-binding proteins (RBPs; also referred to as extractable nuclear antigens) were first characterized in SLE over 40 years ago (Holman, *Ann N Y Acad. Sci.* 124(2):800-6 (1965)). Such RBPs comprise a group of proteins—SSA (Ro52/TRIM21 and Ro60/TROVE2), SSB (La), U1 small nuclear ribonucleoprotein (RNP) protein and Smith (Sm) protein—with roles in RNA processing and biochemistry. Anti-SSA—and anti-SSB IgG autoAbs are found not only in SLE, but also Sjögren's and rheumatoid arthritis syndrome. Anti-SSA autoAbs are associated with subacute cutaneous lupus erythematosus, and with congenital heart block and neonatal lupus in children of anti-SSA positive women. Anti-SSB autoAbs are nearly always found together with anti-SSA autoAbs, and both autoantigens associate with cytoplasmic hYRNA (Lerner et al., *Science* 211(4480):400-2 (1981)). Anti-Sm autoAbs are highly specific for SLE and are generally found together with anti-RNP autoAbs. Both Sm and RNP proteins associate with specific snRNA species in the nuclear RNA spliceosome (Lerner et al., *Proc Natl Acad Sci USA* 76(11):5495-9 (1979)). Anti-RNP autoAbs are also found in patients with mixed connective tissue disease. It has been suggested that the presence of anti-RBP autoAbs may identify SLE cases that show less durable responses following B cell depletion therapy (Cambridge et al., *Ann Rheum Dis* 67:1011-16 (2008)).

Prior art discloses medicines for the treatment of autoimmune diseases. For instance, both international applications WO 03/020747 and WO 03/025014 disclose a fragment of snRNP 70 kDa, which is modified by phosphorylation and/or by acetylation, for treating such pathologies, i.e. autoimmune disease. However, further experimentation has indicated that the peptides disclosed in WO 03/020747 and WO 03/025014 are relatively unstable and rapidly eliminated when administered to mammals. Moreover, some of the disclosed peptides are inactive.

Therefore, there is a need to provide a better treatment for auto-immune pathologies.

SUMMARY

The present description provides compositions and methods of using the same that are based on the surprising and unexpected discovery that certain modified forms of the peptide of SEQ ID NO:2 are more stable when administered to mammals. Thus, in one aspect the present description provides compositions comprising the same and a pharmaceutically acceptable carrier.

In another aspect, the present description provides a pharmaceutical composition, or drug, useful for amelioration of auto-immune diseases, advantageously for the treatment of lupus.

In an additional aspect, the present description provides methods for treating an auto-immune disease comprising administering an effective amount of a therapeutic composition as described herein.

In certain embodiments, the description provides an isolated peptide (recombinant or synthesized), or a salt thereof, comprising or consisting of the amino acid sequence:

IHMVYSKRSGKPRGYAFIEY, [SEQ ID NO: 2]

in which the Serine (S) at position 9 is phosphorylated, and the Methionine (M) at position 3 is oxidized.

In certain embodiments, the description provides a peptide of compound I having the following formula:

sisting of phosphorylation of a serine residue, oxidation of a methionine residue, and acetylation of a lysine residue, and combinations thereof. In an embodiment of this aspect, the description provides a composition comprising an isolated peptide having or consisting of the amino acid sequence of SEQ ID NO: 1, or salt thereof, wherein the peptide comprises a phosphoserine at position 10, and an oxidized Methionine residue at position 4. In certain additional embodiments, the peptide of SEQ ID NO:1 also comprises an acetylated lysine residue. In particular, said peptide of SEQ ID NO: 1 comprises a phosphoserine at position 10, and an oxidized Methionine residue at position 4, and an acetylation of one or both of the lysine at position 8 and 12, and more particularly further comprises a phosphoserine at position 7.

In additional aspects, the description provides an isolated peptide comprising or consisting of the amino acid sequence of SEQ ID NO: 2, or salt thereof, having at least one post-translational modification selected from the group con-

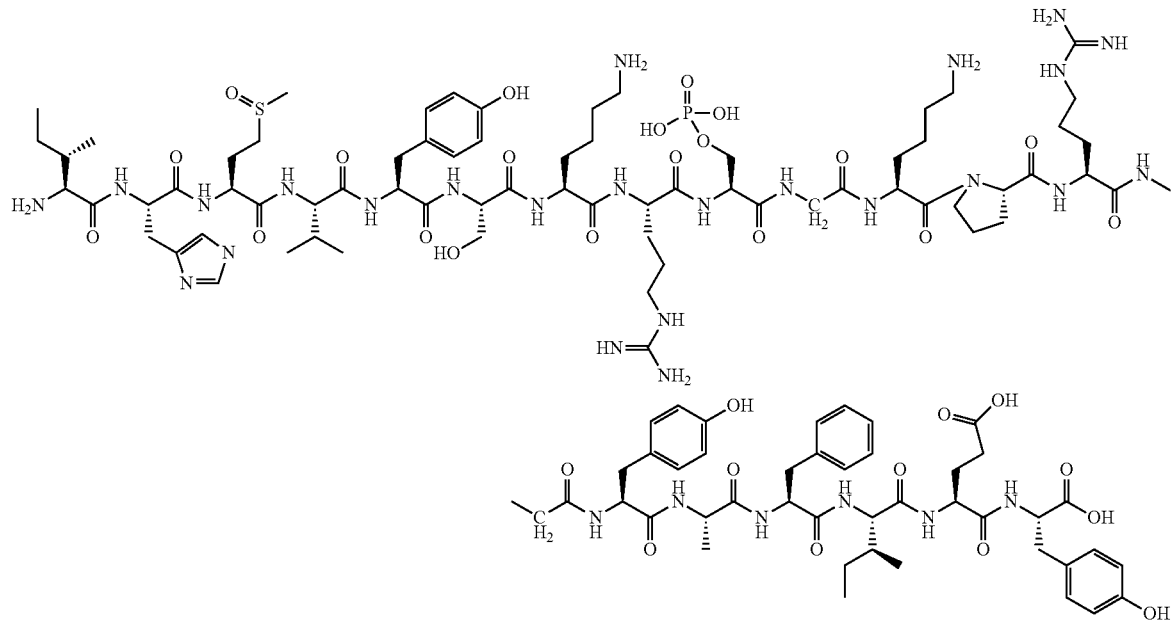

Compound I can also be represented by:

IHM(O)VYSKRS(PO₃H₂)GKPRGYAFIEY [SEQ ID NO: 5]

in which "M(O)" represents oxidized methionine, and "S(PO₃H₂)" represents phosphoserine.

These peptides are derived from the human U1 snRNP 70 kDa protein (SEQ ID NO: 3), and correspond to the region delimited by the amino acid segment extending from the residue 132 to the residue 151 of SEQ ID NO: 3. Formally, the residue which is phosphorylated corresponds to the amino acid at the position 140 from the first methionine of SEQ ID NO: 3, and the residue which is oxidized corresponds to the amino acid at the position 134 from the first methionine of SEQ ID NO: 3.

In certain aspects, the description provides an isolated peptide comprising or consisting of the amino acid sequence of SEQ ID NO: 1, or salt thereof, having at least one post-translational modification selected from the group consisting of phosphorylation of a serine residue, oxidation of a methionine residue, and acetylation of a lysine residue, and combinations thereof. In an embodiment of this aspect, the description provides a composition comprising an isolated peptide having or consisting of the amino acid sequence of SEQ ID NO: 2, or salt thereof, wherein the peptide comprises a phosphoserine at position 9, and an oxidized Methionine residue at position 3. In certain additional embodiments, the peptide of SEQ ID NO:2 also comprises an acetylated lysine residue.

In certain aspects, the description provides a composition comprising an effective amount of one or more of the peptides as described herein. In certain embodiments, the composition further comprises a pharmaceutically acceptable carrier. In an additional embodiment, the description provides a composition comprising an effective amount of at least one peptide, or salt thereof, selected from the group consisting of the amino acid sequence SEQ ID NO: 2, comprising a phosphoserine at position 9, and oxidized Methionine at position 3; the amino acid sequence SEQ ID NO: 1, comprising a phosphoserine at position 10, and an oxidized Methionine at position 4; and a combination of both.

In certain embodiments, the description provides a peptide of compound II having the following formula:

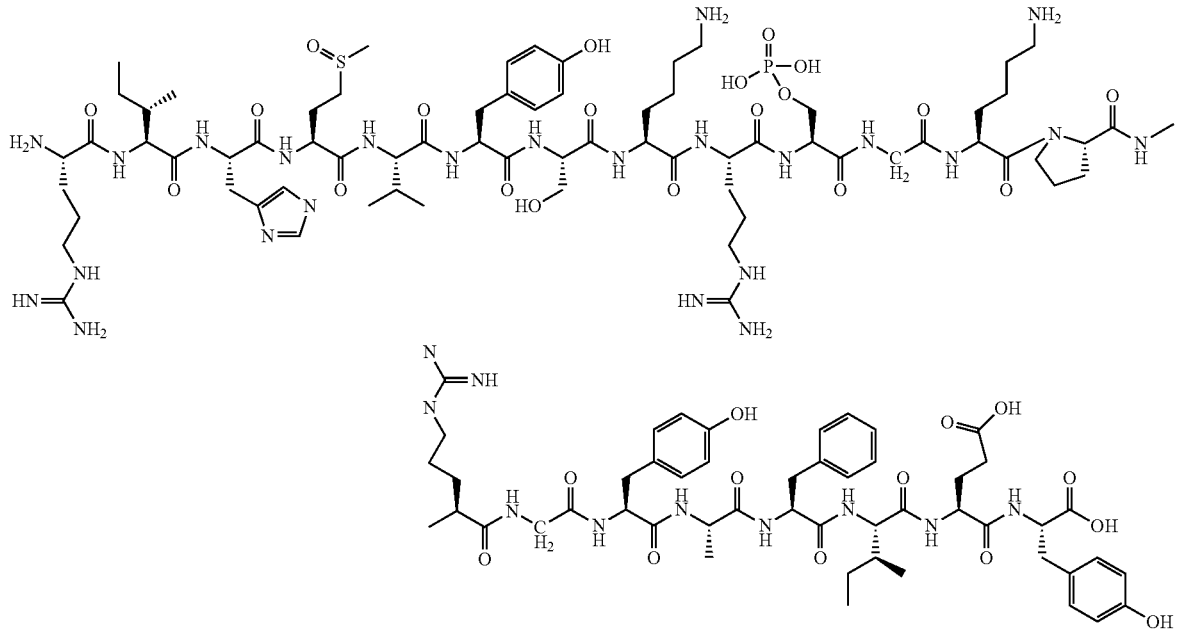

Compound II can also be represented by:

[SEQ ID NO: 4]
RIHM(O)VYSKRS(PO₃H₂)GKPRGYAFIEY in which M(O) represents oxidation of methionine, and S(PO₃H₂) represents the phosphorylation of serine.

Thus, the description provides peptides, or a salt thereof, comprising or consisting of the amino acid sequence chosen among the group consisting of SEQ ID NO: 4 and SEQ ID NO: 5.

The Invention will be better illustrated by the following FIGS. 1 to 6, the accompanying description, examples, and the appended claims, all of which illustrate various exemplary embodiment(s) of the invention and are not to be construed as limiting the invention.

BRIEF DESCRIPTION OF THE DRAWINGS

The accompanying drawings, which are incorporated into and form a part of the specification, illustrate several embodiments of the present invention and, together with the description, serve to explain the principles of the invention. The drawings are only for the purpose of illustrating an embodiment of the invention and are not to be construed as limiting the invention.

DETAILED DESCRIPTION

Figure 1:
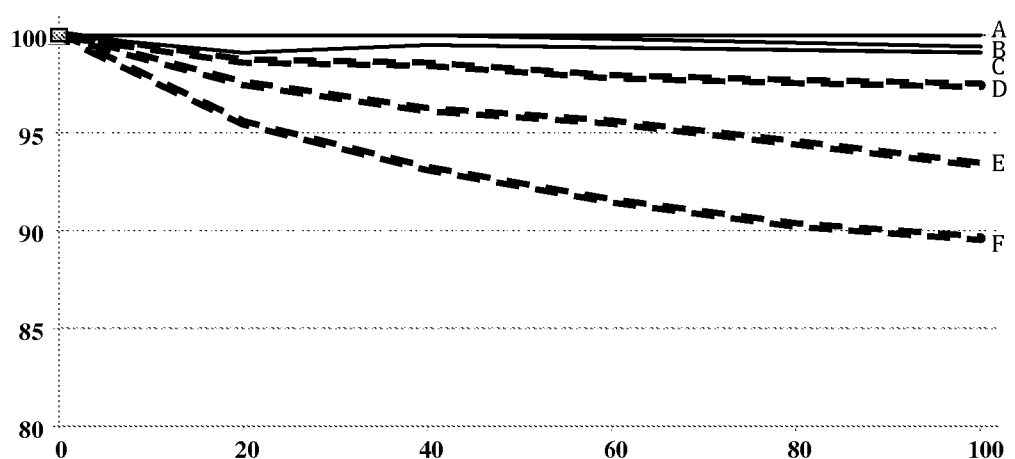
FIG. 1 represents the stability at 37° C. of the peptide according to the invention (Compound II) compared to the stability of the peptide consisting of SEQ ID NO: 1, in which serine at position 10 is phosphorylated. The graph represents the percentage of stability over the time (expressed in days). Curves A-C represent the stability of Compound II at a concentration of 200, 100 and 50 µg/ml, respectively. Curves D-F represent the stability of the peptide consisting of SEQ ID NO: 1, in which serine at position 10 is phosphorylated at a concentration of 200, 100 and 50 µg/ml, respectively.

The following is a detailed description of the invention provided to aid those skilled in the art in practicing the present invention. Those of ordinary skill in the art may make modifications and variations in the embodiments described herein without departing from the spirit or scope of the present invention. Although any methods and materials similar or equivalent to those described herein can also be used in the practice or testing of the present invention, the preferred methods and materials are now described. Unless otherwise defined, all technical and scientific terms used herein have the same meaning as commonly understood by one of ordinary skill in the art to which this invention belongs. The terminology used in the description of the invention herein is for describing particular embodiments only and is not intended to be limiting of the invention. All publications, patent applications, patents, figures and other references mentioned herein are expressly incorporated by reference in their entirety.

As used herein, the following terms may have meanings ascribed to them below, unless specified otherwise. However, it should be understood that other meanings that are known or understood by those having ordinary skill in the art are also possible, and within the scope of the present invention.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges which may independently be included in the smaller ranges is also encompassed within the invention, subject to any specifically excluded limit in the stated range. Where the stated range includes one or both of the limits, ranges excluding either both of those included limits are also included in the invention.

It must be noted that as used herein and in the appended claims, the singular forms "a", "and", and "the" include plural references (i.e., refer to one or to more than one or at least one) to the grammatical object of the article. By way of example, "an element" means one element or more than one element.

The term "about" as it is used herein, in association with numeric values or ranges, reflects the fact that there is a certain level of variation that is recognized and tolerated in the art due to practical and/or theoretical limitations. For example, minor variation is tolerated due to inherent variances in the manner in which certain devices operate and/or measurements are taken. In accordance with the above, the phrase "about" is normally used to encompass values within the standard deviation or standard error.

As used herein, "derivatives" are compositions formed from the native compounds either directly, by modification, or by partial substitution. As used herein, "analogs" are compositions that have a structure similar to, but not identical to, the native compound.

The term "effective amount/dose," "pharmaceutically effective amount/dose," "pharmaceutically effective amount/dose" or "therapeutically effective amount/dose" can mean, but is in no way limited to, that amount/dose of the active pharmaceutical ingredient sufficient to prevent, inhibit the occurrence, ameliorate, delay or treat (alleviate a symptom to some extent, preferably all) the symptoms of a condition, disorder or disease state. The effective amount depends on the type of disease, the composition used, the route of administration, the type of mammal being treated, the physical characteristics of the specific mammal under consideration, concurrent medication, and other factors which those skilled in the medical arts will recognize.

Generally, an amount between 0.1 mg/kg and 1000 mg/kg body weight/day of active ingredients is administered dependent upon potency of the agent. Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds that exhibit large therapeutic indices are preferred. While compounds that exhibit toxic side effects may be used, care should be taken to design a delivery system that targets such compounds to the site of affected tissue in order to minimize potential damage to uninfected cells and, thereby, reduce side effects. The data obtained from the cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

The term "pharmacological composition," "therapeutic composition," "therapeutic formulation" or "pharmaceutically acceptable formulation" can mean, but is in no way limited to, a composition or formulation that allows for the effective distribution of an agent provided by the invention, which is in a form suitable for administration to the physical location most suitable for their desired activity, e.g., systemic administration.

The term "pharmaceutically acceptable" or "pharmacologically acceptable" can mean, but is in no way limited to, entities and compositions that do not produce an adverse, allergic or other untoward reaction when administered to an animal, or a human, as appropriate.

The term "pharmaceutically acceptable carrier" or "pharmacologically acceptable carrier" can mean, but is in no way limited to, any and all solvents, dispersion media, coatings, antibacterial and antifungal agents, isotonic and absorption delaying agents, and the like, compatible with pharmaceutical administration. Suitable carriers are described in the most recent edition of Remington's Pharmaceutical Sciences, a standard reference text in the field, which is incorporated herein by reference. Preferred examples of such carriers or diluents include, but are not limited to, water, saline, finger's solutions, dextrose solution, and 5% human serum albumin. Liposomes and non-aqueous vehicles such as fixed oils may also be used. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

The term "systemic administration" refers to a route of administration that is, e.g., enteral or parenteral, and results in the systemic distribution of an agent leading to systemic absorption or accumulation of drugs in the blood stream followed by distribution throughout the entire body. Suitable forms, in part, depend upon the use or the route of entry, for example oral, transdermal, or by injection. Such forms should not prevent the composition or formulation from reaching a target cell (i.e., a cell to which the negatively charged polymer is desired to be delivered to). For example, pharmacological compositions injected into the blood stream should be soluble. Other factors are known in the art, and include considerations such as toxicity and forms which prevent the composition or formulation from exerting its effect. Administration routes which lead to systemic absorption include, without limitations: intravenous, subcutaneous, intraperitoneal, inhalation, oral, intrapulmonary and intramuscular. The rate of entry of a drug into the circulation has been shown to be a function of molecular weight or size. The use of a liposome or other drug carrier comprising the compounds of the instant invention can potentially localize the drug, for example, in certain tissue types, such as the tissues of the reticular endothelial system (RES). A liposome formulation which can facilitate the association of drug with the surface of cells, such as, lymphocytes and macrophages is also useful.

The term "local administration" refers to a route of administration in which the agent is delivered to a site that is apposite or proximal, e.g., within about 10 cm, to the site of the lesion or disease.

The term "derivatives" can mean, but is in no way limited to, chemical compositions, for example, nucleic acids, nucleotides, polypeptides or amino acids, formed from the native compounds either directly, by modification, or by partial substitution. The term "analogs" can mean, but is in no way limited to, chemical compositions, for example, nucleic acids, nucleotides, polypeptides or amino acids that have a structure similar to, but not identical to, the native compound.

The term "conservative mutations" refers to the substitution, deletion or addition of nucleic acids that alter, add or delete a single amino acid or a small number of amino acids in a coding sequence where the nucleic acid alterations result in the substitution of a chemically similar amino acid. Amino acids that may serve as conservative substitutions for each other include the following: Basic: Arginine (R), Lysine (K), Histidine (H); Acidic: Aspartic acid (D), Glutamic acid (E), Asparagine (N), Glutamine (Q); hydrophilic: Glycine (G), Alanine (A), Valine (V), Leucine (L), Isoleucine (I); Hydrophobic: Phenylalanine (F), Tyrosine (Y), Tryptophan (W); Sulfur-containing: Methionine (M), Cysteine (C). In addition, sequences that differ by conservative variations are generally homologous.

By "homology" is meant the nucleotide sequence of two or more nucleic acid molecules or two or more nucleic acid or amino acid sequences is partially or completely identical. In certain embodiments the homologous nucleic acid or amino acid sequence has 30%, 40%, 50%, 60%, 70%, 80%, 90%, or 95% sequence similarity or identity to an nucleic acid encoding the amino acid sequence of SEQ ID NO:1 or SEQ ID NO:1, respectively.

"Homologs" can be naturally occurring, or created by artificial synthesis of one or more nucleic acids having related sequences, or by modification of one or more nucleic acid to produce related nucleic acids. Nucleic acids are homologous when they are derived, naturally or artificially, from a common ancestor sequence (e.g., orthologs or paralogs). If the homology between two nucleic acids is not expressly described, homology can be inferred by a nucleic acid comparison between two or more sequences. If the sequences demonstrate some degree of sequence similarity, for example, greater than about 30% at the primary amino acid structure level, it is concluded that they share a common ancestor. For purposes of the present invention, genes are homologous if the nucleic acid sequences are sufficiently similar to allow recombination and/or hybridization under low stringency conditions. In addition, polypeptides are regarded as homologous if their nucleic acid sequences are sufficiently similar to allow recombination or hybridization under low stringency conditions, and optionally they demonstrate membrane repair activity, and optionally they can be recognized by (i.e., cross-react with) an antibody specific for an epitope contained within the amino acid sequence of at least one of SEQ ID NOs: 1-6.

The term "cell" can mean, but is in no way limited to, its usual biological sense, and does not refer to an entire multicellular organism. The cell can, for example, be in vivo, in vitro or ex vivo, e.g., in cell culture, or present in a multicellular organism, including, e.g., birds, plants and mammals such as humans, cows, sheep, apes, monkeys, swine, dogs, and cats. The cell can be prokaryotic (e.g., bacterial cell) or eukaryotic (e.g., mammalian or plant cell).

The term "host cell" can mean, but is in no way limited to, a cell that might be used to carry a heterologous nucleic acid, or expresses a peptide or protein encoded by a heterologous nucleic acid. A host cell can contain genes that are not found within the native (non-recombinant) form of the cell, genes found in the native form of the cell where the genes are modified and re-introduced into the cell by artificial means, or a nucleic acid endogenous to the cell that has been artificially modified without removing the nucleic acid from the cell. A host cell may be eukaryotic or prokaryotic. General growth conditions necessary for the culture of bacteria can be found in texts such as BERGEY'S MANUAL OF SYSTEMATIC BACTERIOLOGY, Vol. 1, N. R. Krieg, ed., Williams and Wilkins, Baltimore/London (1984). A "host cell" can also be one in which the endogenous genes or promoters or both have been modified to produce one or more of the polypeptide components of the complex of the invention.

As used herein, "P140" refers to a peptide consisting of the amino acid sequence SEQ ID NO: 1, in which serine at position 10 is phosphorylated.

The term "therapeutically effective amount or dose" includes a dose of a drug that is capable of achieving a therapeutic effect in a subject in need thereof. For example, a therapeutically effective amount of a drug can be the amount that is capable of preventing or relieving one or more symptoms associated with a disease or disorder, e.g., tissue injury or muscle-related disease or disorder. The exact amount can be ascertainable by one skilled in the art using known techniques (see, e.g., Lieberman, Pharmaceutical Dosage Forms (vols. 1-3, 1992); Lloyd, The Art, Science and Technology of Pharmaceutical Compounding (1999); Pickar, Dosage Calculations (1999); and Remington: The Science and Practice of Pharmacy, 20th Edition, 2003, Gennaro, Ed., Lippincott, Williams & Wilkins).

A kit is any manufacture (e.g. a package or container) comprising at least one reagent, e.g. a probe, for specifically detecting a marker of the invention. The manufacture may be promoted, distributed, or sold as a unit for performing the methods of the present invention. The reagents included in such a kit comprise probes/primers and/or antibodies for use in detecting sensitivity and resistance gene expression. In addition, the kits of the present invention may preferably contain instructions which describe a suitable detection assay. Such kits can be conveniently used, e.g., in clinical settings, to diagnose patients exhibiting symptoms of cancer, in particular patients exhibiting the possible presence of a tumor.

Unless otherwise defined, all technical and scientific terms used herein have the same meaning as commonly understood by one of ordinary skill in the art to which this invention belongs. All publications, patent applications, patents, and other references mentioned herein are incorporated by reference in their entirety. In the case of conflict, the present specification, including definitions, will control. In addition, the materials, methods, and examples are illustrative only and not intended to be limiting.

The following references, the entire disclosures of which are incorporated herein by reference, provide one of skill with a general definition of many of the terms used in this invention: Singleton et al., Dictionary of Microbiology and Molecular Biology ($2^{nd}$ ed. 1994); The Cambridge Dictionary of Science and Technology (Walker ed., 1988); The Glossary of Genetics, $5^{th}$ Ed., R. Rieger et al. (eds.), Springer Verlag (1991); and Hale & Marham, the Harper Collins Dictionary of Biology (1991).

The present description provides compositions and methods of using the same that are based on the surprising and unexpected discovery that certain modified forms of the peptide of SEQ ID NO:2 are stable when administered to mammals. Thus, in one aspect the present description provides compositions comprising the same and a pharmaceutically acceptable carrier.

In another aspect, the present description provides a pharmaceutical composition, or drug, useful for amelioration of auto-immune diseases, advantageously for the treatment of lupus.

In an additional aspect, the present description provides methods for treating an auto-immune disease comprising administering an effective amount of a therapeutic composition as described herein.

In certain embodiments, the description provides an isolated peptide (recombinant or synthesized), or a salt thereof, comprising or consisting of the amino acid sequence:

[SEQ ID NO: 2]
IHMVYSKRSGKPRGYAFIEY, in which the Serine (S) at position 9 is phosphorylated, and the Methionine (M) at position 3 is oxidized.

In certain embodiments, the description provides a peptide of compound I having the following formula:

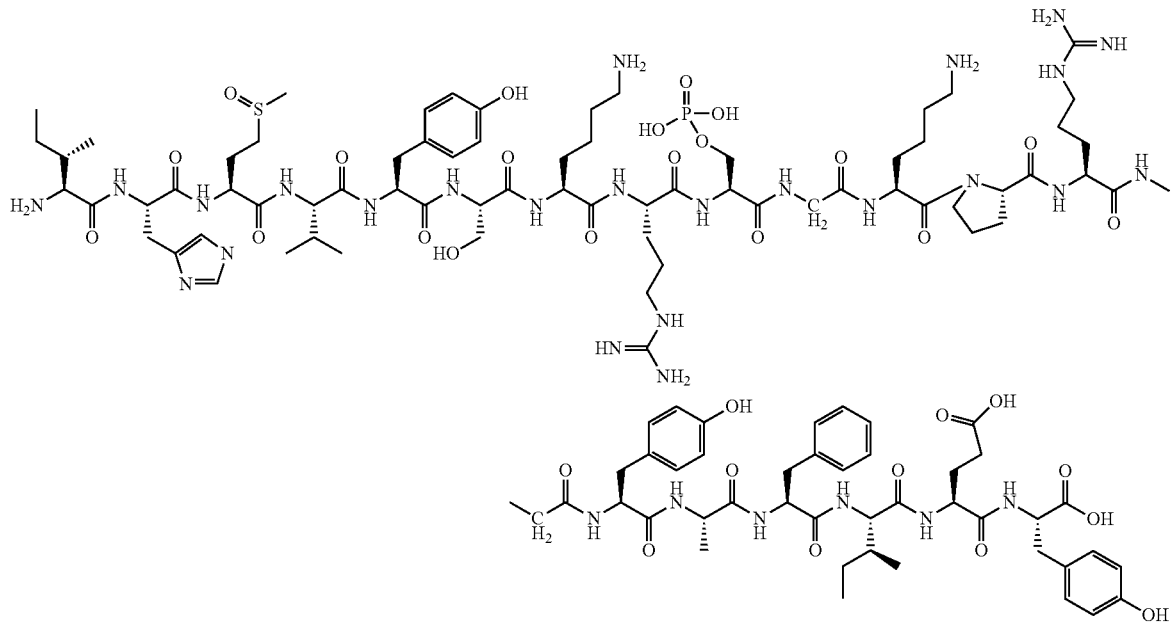

Compound I can also be represented by:

[SEQ ID NO: 5]
IHM(O)VYSKRS(PO3H2)GKPRGYAFIEY in which "M(O)" represents oxidized methionine, and "S(PO$_3$H$_2$)" represents phosphoserine.

These peptides are derived from the human U1 snRNP 70 kDa protein (SEQ ID NO: 3), and correspond to the region delimited by the amino acid segment extending from the residue 132 to the residue 151 of SEQ ID NO: 3. Formally, the residue which is phosphorylated corresponds to the amino acid at the position 140 from the first methionine of SEQ ID NO: 3, and the residue which is oxidized corresponds to the amino acid at the position 134 from the first methionine of SEQ ID NO: 3.

In certain aspects, the description provides an isolated peptide comprising or consisting of the amino acid sequence of SEQ ID NO: 1, or salt thereof, having at least one post-translational modification selected from the group consisting of phosphorylation of a serine residue, oxidation of a methionine residue, and acetylation of a lysine residue, and combinations thereof. In an embodiment of this aspect, the description provides a composition comprising an isolated peptide having or consisting of the amino acid sequence of SEQ ID NO: 1, or salt thereof, wherein the peptide comprises a phosphoserine at position 10, and an oxidized Methionine residue at position 4. In certain additional embodiments, the peptide of SEQ ID NO:1 also comprises an acetylated lysine residue.

In additional aspects, the description provides an isolated peptide comprising or consisting of the amino acid sequence of SEQ ID NO: 2, or salt thereof, having at least one post-translational modification selected from the group consisting of phosphorylation of a serine residue, oxidation of a methionine residue, and acetylation of a lysine residue, and combinations thereof. In an embodiment of this aspect, the description provides a composition comprising an isolated peptide having or consisting of the amino acid sequence of SEQ ID NO: 2, or salt thereof, wherein the peptide comprises a phosphoserine at position 9, and an oxidized Methionine residue at position 3. In certain additional embodiments, the peptide of SEQ ID NO:2 also comprises an acetylated lysine residue.

In certain aspects, the description provides a composition comprising an effective amount of one or more of the peptides as described herein. In certain embodiments, the composition further comprises a pharmaceutically acceptable carrier. In an additional embodiment, the description provides a composition comprising an effective amount of at least one peptide, or salt thereof, selected from the group consisting of the amino acid sequence SEQ ID NO: 2, comprising a phosphoserine at position 9, and oxidized Methionine at position 3; the amino acid sequence SEQ ID NO: 1, comprising a phosphoserine at position 10, and an oxidized Methionine at position 4; and a combination of both.

In certain embodiments, the description provides a peptide of compound II having the following formula:

in which M(O) represents the oxidation, and S(PO$_3$H$_2$) represents the phosphorylation.

The description provides peptides, and/or salts thereof, comprising or consisting of the amino acid sequence chosen among the group consisting of SEQ ID NO: 4, SEQ ID NO: 5, and combinations thereof, as well as compositions comprising the same.

In certain embodiments, the description provides an isolated peptide having the amino acid sequence of SEQ ID NO: 1, comprising a phosphoserine at position 10, and an oxidized methionine at position 4 (e.g., SEQ ID NO: 4) (herein, also referred to as Compound II or P140(MO)).

According to the present description, the isolated peptides having the amino acid sequence of SEQ ID NO: 4 or 5, respectively, are modified by at least two post-translational modifications (modifications that occur after the synthesis of the peptides). In certain embodiments, the post-translational modification is selected from the group consisting of phosphorylation (addition of a phosphate PO$_3$H$_2$), e.g., phosphorylation of a serine residue; oxidation, e.g., oxidation of a methionine residue; acetylation, e.g., acetylation of a lysine residue; and combinations thereof.

In a preferred embodiment, the description provides an isolated peptide having the amino acid sequence as set forth in SEQ ID NO: 2 comprising a phosphoserine at position 9 and an oxidized methionine at position 3, or salt thereof. In certain embodiments, the description provides the peptide having the amino acid sequence as set forth in SEQ ID NO: 2, comprising a phosphoserine at position 9 and an oxidized methionine at position 3, or salt thereof, and a carrier, e.g., a pharmaceutically acceptable carrier. In certain additional embodiments, the description provides a composition, e.g., a therapeutic composition, comprising an effective amount

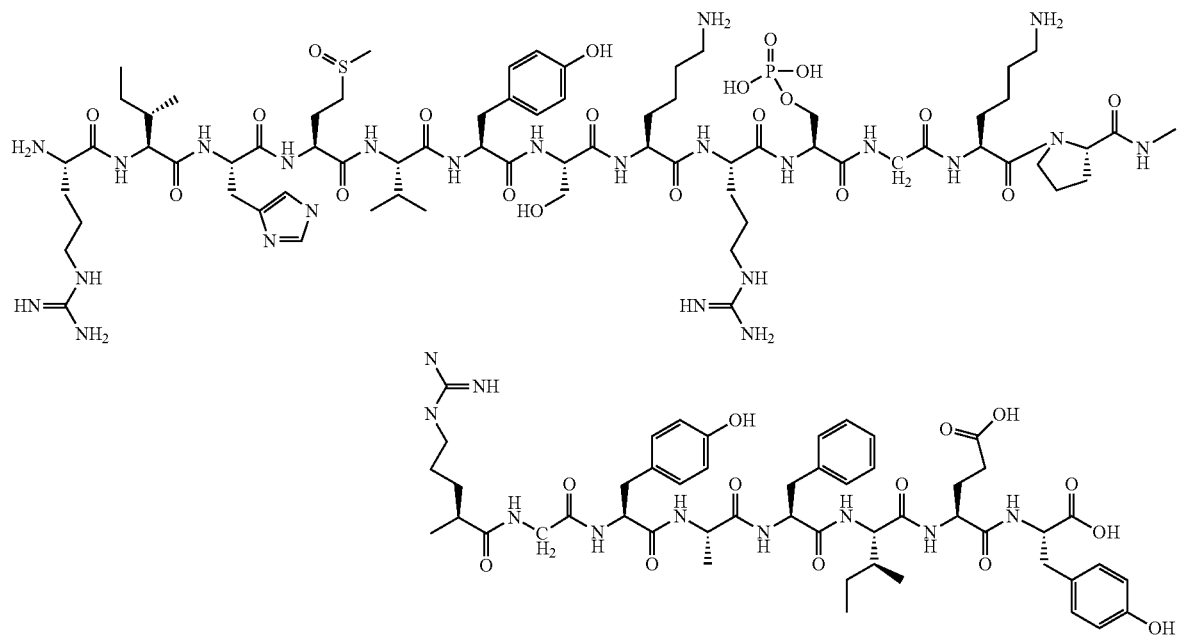

Compound II can also be represented by:

[SEQ ID NO: 4]
RIHM(O)VYSKRS(PO$_3$H$_2$)GKPRGYAFIEY of a peptide having the amino acid sequence as set forth in SEQ ID NO: 2, comprising a phosphoserine at position 9 and an oxidized methionine at position 3, or salt thereof, and a carrier, e.g., a pharmaceutically acceptable carrier.

In another embodiment, the description provides an isolated peptide having the amino acid sequence as set forth in SEQ ID NO: 4 comprising a phosphoserine at position 10, and an oxidized methionine at position 4, or salt thereof. In certain embodiments, the description provides the peptide having the amino acid sequence as set forth in SEQ ID NO: 4 comprising a phosphoserine at position 10, and an oxidized methionine at position 4, or salt thereof, and a carrier, e.g., a pharmaceutically acceptable carrier. In certain additional embodiments, the description provides a composition, e.g., a therapeutic composition, comprising an effective amount of a peptide having the amino acid sequence as set forth in SEQ ID NO: 4 comprising a phosphoserine at position 10, or salt thereof, and an oxidized methionine at position 4, and a carrier, e.g., a pharmaceutically acceptable carrier.

In another embodiment, the description provides an isolated peptide having the amino acid sequence as set forth in SEQ ID NO: 5 comprising a phosphoserine at position 9 and an oxidized methionine at position 3, or salt thereof. In certain embodiments, the description provides the peptide having the amino acid sequence as set forth in SEQ ID NO: 5 comprising a phosphoserine at position 9 and an oxidized methionine at position 3, or salt thereof, and a carrier, e.g., a pharmaceutically acceptable carrier. In certain additional embodiments, the description provides a composition, e.g., a therapeutic composition, comprising an effective amount of a peptide having the amino acid sequence as set forth in SEQ ID NO: 5 comprising a phosphoserine at position 9 and an oxidized methionine at position 3, or salt thereof, and a carrier, e.g., a pharmaceutically acceptable carrier.

Surprisingly and unexpectedly, it was discovered that the peptides as described herein are more stable in vitro compared to the non-oxidized counterpart. The stability is measured as disclosed in the example section. The phosphorylated-oxidized peptide is less spontaneously degraded in solution compared to the non-oxidized counterpart, said stability enhancing its biological properties.

In addition, the inventors have surprisingly identified that the methionine oxidation enhances the peptide stability, without affecting the biological effect of such peptide, contrary to the teaching of the prior art. Indeed, it is largely reported in the art that proteins or peptides containing oxidized methionine have disruptions in their three-dimensional structure and/or bioactivity. The modified peptides as described herein have an affinity for HSC70 protein essentially identical to the non-oxidized counterpart as disclosed in the example section.

In certain embodiments, the oxidation occurs in the Methionine (M) at position 9 of SEQ ID NO: 2, or at position 10 of SEQ ID NO: 1, which are the equivalent positions to the position 134 of SEQ ID NO: 3. The sulfur atom is oxidized as illustrated below.

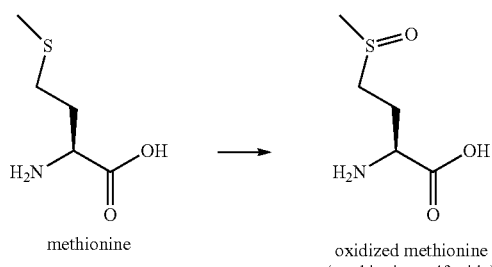
methionine → oxidized methionine (methionine sulfoxide)

The above peptides (SEQ ID NO: 1, 2, 4 and 5) can be synthesized by techniques commonly used in the art, such as biological synthesis or chemical synthesis. Biological synthesis refers to the production, in vivo, in vitro or ex vivo, of the peptide of interest, by the transcription and translation of a nucleic acid molecule coding for said peptides.

For instance the nucleic acid sequence:

[SEQ ID NO: 6]
MGNATHCAYATGGTNTAYWSNAARMGNWSNGGNAARCCNMGNGG

NTAYGCNTTYATHGARTAYTRR is transcribed and translated either in an in vitro system, or in a host organism, in order to produce the peptide SEQ ID NO: 1. The produced peptide is thus purified according to well known techniques.

Chemical synthesis consists to polymerize the desired peptide by adding the required amino acids. A method is disclosed in the example section.

It is possible to chemically synthesize the peptides SEQ ID NO: 1 and 2 by classical Fmoc (N-[9-fluorenyl]methoxycarbonyl) solid-phase chemistry and purified by reversed-phase high-performance liquid chromatography (HPLC; Neimark and Briand, 1993; Monneaux et al., 2003, *Eur. J. Immunol.* 33, 287-296; Page et al., 2009, PloS ONE 4, e5273).

It is also possible to directly synthesize the peptides SEQ ID NO: 1 and 2, in which respective residues at position 10 and 9 are phosphorylated. For this purpose, during the peptide synthesis a Fmoc-Ser(PO(Obz)OH)—OH-type serine derivative was used, at the desired position.

Phosphate group (—$PO_3H_2$) can also be added after the synthesis of the peptide, according to protocols well known in the art.

Serine can be phosphorylated by incubating the peptides SEQ ID NO: 1 or 2 with specific serine kinase chosen among Protein Kinase A or C (PKA or PKC) or casein kinase II, in presence of adenosine triphosphate (ATP). The peptides are thus phosphorylated in one serine (at position 6 or 9 of SEQ ID NO: 2, or at position 7 or 10 of SEQ ID NO: 1), or both serine. The desired phosphorylated peptide is separated from the others for instance by chromatography.

A chemical addition of —$PO_3H_2$ can also be added at the specific position (at position 9 of SEQ ID NO: 2, or at position 10 of SEQ ID NO: 1), by using specific protective group, that the skilled person can easily choose according to his common knowledge.

Any other techniques known in the art, allowing the specific phosphorylation of serine, can be used.

In certain embodiments, the oxidation of Methionine is performed according to the following process:

treating with either with $H_2O_2$, 20 mM, at 37° C. for 4 hours, or in a solution of dimethylsulfoxyde (DMSO; $Me_2SO$), 0.1M plus HCl 0.5 M, at 22° C. for 30 to 180 min.

Any other techniques known in the art, allowing the specific oxidation of methionine, can be used.

In any of the aspects or embodiments described herein, the peptide(s) provided by the description can be present in a form of a salt known to a person skilled in the art, such as, e.g., sodium salts, ammonium salts, calcium salts, magnesium salts, potassium salts, acetate salts, carbonate salts, citrate salts, chloride salts, sulphate salts, amino chlorhydate salts, borhydrate salts, benzensulphonate salts, phosphate salts, dihydrogenophosphate salts, succinate salts, citrate salts, tartrate salts, lactate salts, mandelate salts, methane sulfonate salts (mesylate) or p-toluene sulfonate salts (tosylate). This list is provided by way of example and is not meant to be limiting on the present invention. For example, the skilled person can easily determine, according to his knowledge, the appropriate salt.

In an additional embodiment, the description provides a peptide comprising or consisting of the amino acid sequence:

RIHMVYSKRSGKPRGYAFIEY, [SEQ ID NO: 1]

comprising a phosphoserine at position 10, and an oxidized Methionine at position 4, or salt thereof. In one advantageous embodiment, the invention relates to the peptide as defined above, consisting of the amino acid sequence SEQ ID NO: 4, or salt thereof.

In another aspect, the description provides a therapeutic composition comprising at least a peptide as described herein, or salt thereof, and a drug having an immunosuppressive effect. In certain embodiments, the therapeutic composition comprises an effective amount of a peptide as described herein, and an effective amount of a drug having an immunosuppressive effect. In one embodiment, the peptide has the amino acid sequence SEQ ID NO: 1, comprising a phosphoserine at position 10, and a drug having an immunosuppressive effect.

The peptide consisting of the amino acid sequence SEQ ID NO: 1, in which the Serine at position 10 is phosphorylated corresponds to the below Compound III:

mine other known drugs having an immunosuppressive or immunomodulating effect, their effective amounts, and routes of administration.

In certain embodiments, the description provides a therapeutic composition comprising an effective amount of a peptide having the amino acid sequence as set forth in at least one of SEQ ID NO: 4, 5, or a combination thereof (i.e., comprising peptides of SEQ ID NO: 5, and SEQ ID NO: 4), and an effective amount of a drug having an immunosuppressive or immunomodulating effect. In additional embodiment, the composition may additionally comprise a peptide having the amino acid sequence as set forth in SEQ ID NO: 1, comprising a phosphoserine at position 10.

In an additional aspect, the description also provides methods of treating an autoimmune disease, comprising the step of administering to a subject (e.g., a patient such as a mammal, e.g., a human) in need of such treatment an effective amount of a pharmaceutical composition as described herein, wherein the composition is sufficient to effectuate said treatment. In another aspect, the description provides a composition as described herein for use in a method for treating an autoimmune disease comprising the step of administering to a patient in need thereof, an effective amount of a pharmaceutical composition as described herein, wherein the composition is sufficient to effectuate said treatment.

In certain embodiments, the autoimmune disease is chosen among: autoimmune pathologies of the family of connective tissue diseases (non-specific systemic organ dis-

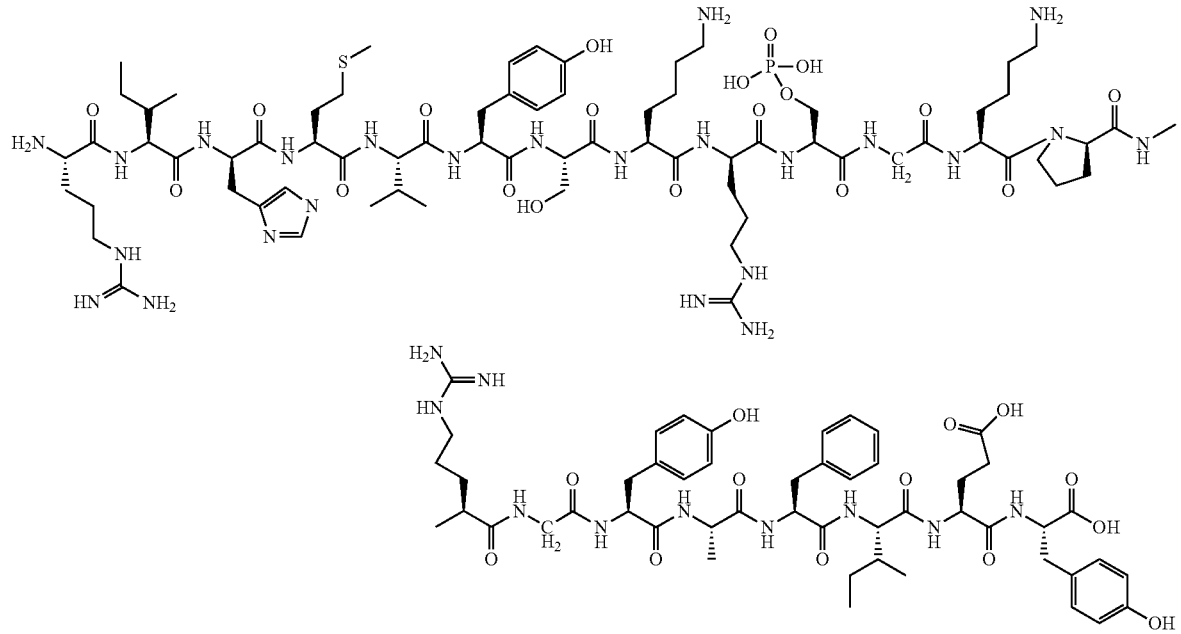

As used herein, "a drug having an immunosuppressive or an immunomodulatory effect" is a drug that inhibits or prevents the activity of a subject's (e.g., a mammal such as a human) immune system. For example, drugs "having an immunosuppressive effect," include: corticoids such as methyl prednisolone; cyclophosphamides; azathioprines; hydroxychloroquines; antimalarials; mycophenolate mofetil; methotrexate; biologics, e.g., infliximab, etanercept, golimumab, adalimumab, certolizumab; and combinations of the above. This list is not intended to be limiting on the invention. For example, the skilled person can easily detereases), e.g., systemic lupus erythematosus (SLE), rheumatoid arthritis, mixed connective tissue disease, Sjögren's syndrome, or chronic juvenile arthritis; and/or organ-specific autoimmune pathologies, e.g., multiple sclerosis, insulin-dependent diabetes, Crohn's disease, or bullous diseases. In a preferred embodiment, the autoimmune disease is SLE.

The description also provides a drug comprising a peptide as described herein, and/or a combination as described herein, for its use as drug, in particular for the treatment of autoimmune diseases.

In certain embodiments, the autoimmune disease is chosen among: autoimmune pathologies of the family of connective tissue diseases (non-specific systemic organ diseases), e.g., systemic lupus erythematosus (SLE), rheumatoid arthritis, mixed connective tissue disease, Sjögren's syndrome, or chronic juvenile arthritis; and/or organ-specific autoimmune pathologies, e.g., multiple sclerosis, insulin-dependent diabetes, Crohn's disease, or bullous diseases. In a preferred embodiment, the autoimmune disease is SLE.

The description also provides pharmaceutical compositions comprising at least a peptide as described herein, or a combination product as described above, further including a pharmaceutically acceptable carrier.

The peptides (also referred to herein as "active compounds") as described herein can be incorporated into pharmaceutical compositions suitable for administration. Such compositions typically comprise peptide and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

The description provides methods for preparing pharmaceutical compositions. Such methods comprise formulating a pharmaceutically acceptable carrier with a peptide as described herein. Such compositions can further include additional active agents as described above. Thus, the invention further includes methods for preparing a pharmaceutical composition by formulating a pharmaceutically acceptable carrier with a peptide as described herein, and one or more additional active compounds.

A pharmaceutical composition of the invention is formulated to be compatible with its intended route of administration. Examples of routes of administration include parenteral, e.g., intravenous, intradermal, subcutaneous, oral, nasal (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol; antioxidants such as ascorbic acid or sodium bisulfate; chelating agents such as ethylenediamine-tetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersions. For intravenous administration, suitable carriers include physiological saline, bacteriostatic water, Cremophor EL (BASF; Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, chlorobutanol, phenol, ascorbic acid, and the like. In many cases, it will be preferable to include isotonic agents, for example, sugars, polyalcohols such as mannitol, sorbitol, or sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound (e.g., a polypeptide or antibody) in the required amount in an appropriate solvent with one or a combination of ingredients enumerated above, as required, followed by filtered sterilization. Generally, dispersions are prepared by incorporating the active compound into a sterile vehicle which contains a basic dispersion medium, and then incorporating the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed For administration by inhalation, the compounds are delivered in the form of an aerosol spray from a pressurized container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes having monoclonal antibodies incorporated therein or thereon) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

In certain embodiments of the methods provided herein, the method includes the step of administering a dosage from about 100 ng to about 5 mg of a therapeutic or pharmaceutical composition as described herein. In certain embodiments, e.g., in human, the pharmaceutical composition as described herein may contain mannitol as carrier, and the composition is administered from 10 µg to 500 µg, preferably 200 µg, in a single administration.

In certain additional aspects, the dosage regimen can be reproduced from 1 to 3 times/week, every week to every four week. for as long as needed with therapeutic windows and thus for several years. In a preferred embodiment, the dosage regimen is 12 weeks of treatment but can be repeated twice a year for several years. An example of administration is: one injection of 200 µg of peptide, every 4 weeks, for 12 weeks (i.e. 3 injections separated from each other by 4 weeks).

The treatment can be prolonged by administration every 6 months.

Preferred pharmaceutically acceptable carriers can comprise, for example, xanthan gum, locust bean gum, galactose, other saccharides, oligosaccharides and/or polysaccharides, starch, starch fragments, dextrins, British gum and mixtures thereof. Advantageously, the pharmaceutically acceptable carrier is of natural origin. The pharmaceutically acceptable carrier can be, or can further comprise, an inert saccharide diluent selected from a monosaccharide or disaccharide. Advantageous saccharide is mannitol.

Advantageously, the invention relates to a pharmaceutical composition as defined above, which is in the form of a lozenge, tablet, gelatin, capsule, drop, pill, liposome, or nano particles, or in the form of a solution. An advantageous solution is a solution comprising from 5 to 15%, in particular about 10% of mannitol. The solution should be isooasmolar.

The invention also relates to a drug comprising a combination product as defined above, for a simultaneous, separate or sequential use.

EXAMPLES

Statistics

Statistical tests were performed using GraphPad Prism version 5.0. The two-way ANOVA test was used to analyze statistical significance of proteinuria differences between control and peptide-treated groups of mice. Survival of control and P140 analogue-treated female MRL/lpr mice was analyzed by the Kaplan-Meier method, and the significance of differences was determined by the log-rank test. For the other variables, statistical significance was assessed using the Student's t-test. p values less than 0.05 were considered significant.

Example 1

Chemical Synthesis of the Peptides

P140 peptide and P140(MO) were synthesized using classical Fmoc (N-[9-fluorenyl]methoxycarbonyl) solid-phase chemistry and purified by reversed-phase high-performance liquid chromatography (HPLC; Neimark and Briand, 1993; Monneaux et al., 2003, Eur. J. Immunol. 33, 287-296; Page et al., 2009, PloS ONE 4,e5273). Their homogeneity was checked by analytical HPLC, and their identity was assessed by LC/MS on a Finnigan LCQ Advantage Max system (Thermo Fischer Scientific). After completion of the reaction, the peptides were purified by HPLC.

In order to introduce the phosphorylation at the serine residue equivalent to the residue 140 of SEQ ID NO: 3, an Fmoc-Ser(PO(Obz)OH)—OH-type serine derivative was used. The coupling time is increased to 30 minutes and a second coupling is carried out systematically. After cleavage in acid medium, each peptide is precipitated by cold ether, solubilized in a solution of water and acetonitrile and finally lyophilized. The peptides are then purified by RP-HPLC, their integrity and their purity has been analyzed by analytic HPLC and by mass spectrometry (Maldi-TOF).

Oxidation is introduced as mentioned above.

Example 2

Stability of the Peptides

The stability of the peptide SEQ ID NO: 2 in which the serine at position 10 is phosphorylated and the methionine at position 4 is oxidized (P140(MO)), and the peptide SEQ ID NO: 1 in which the serine at position 10 is phosphorylated (P140) was measured at 37° C., in a solution of 10% (v/v) mannitol. For each peptide, 3 concentrations have been tested: 200, 100 and 50 µg/mL.

At the indicated time, the integrity of P140 and P140(MO) peptides was measured in saline by high-performance liquid chromatography from the area of the peak corresponding to the intact peptide.

Results are shown in FIG. 1.

The following tables 1 and 2 summarize the results:

TABLE 1

| | | P140(MO) | | | P140 | | |
|---|---|---|---|---|---|---|---|
| | Days | 200 µg/mL | 100 µg/mL | 50 µg/mL | 200 µg/mL | 100 µg/mL | 50 µg/mL |
| Stability (%) | 0 | 100 | 100 | 100 | 100 | 100 | 100 |
| | 20 | 100 | 99.1 | 100 | 98.7 | 97.5 | 95.5 |
| | 40 | 100 | 99.5 | 100 | 98.5 | 96.2 | 93.2 |
| | 60 | — | — | — | 97.9 | 95.5 | 91.5 |
| | 80 | — | — | — | 97.6 | 94.5 | 90.3 |
| | 100 | 100 | 99.1 | 99.4 | 97.4 | 93.4 | 89.6 |

TABLE 2

| | Days | P140(MO) | | | P140 | | |
| --- | --- | --- | --- | --- | --- | --- | --- |
| | | 200 µg/mL | 100 µg/mL | 50 µg/mL | 200 µg/mL | 100 µg/mL | 50 µg/mL |
| Stability (%) | Linear equation | y = 100 | y = −0.0064x + 100.11 | y = −0.0064x + 99.677 | y = −0.0238x + 99.535 | y = −0.0612x + 99.25 | y = −0.099x + 98.299 |
| | Correlation coefficient | N/A | $R^2 = 0.8571$ | $R^2 = 0.4157$ | $R^2 = 0.8854$ | $R^2 = 0.9538$ | $R^2 = 0.9065$ |
| | 95% of stability (predicted) | ∞ | 2 years + 2 months | 2 years | 6 months | 2 months | 1 months |

Stability is measured by using the HPLC peak surface.

P140 M(O) stability remains unchanged (100%, 99.1% and 99.4%) over 100 days at 37° C., for each of the tested concentrations (50 to 200 µg/ml).

P140 stability deacreases over the time and is reduced after 100 days at 37° C. (97.4%, 93.4% et 89.6%) for each of the tested concentrations (50 to 200 µg/ml).

These data demonstrate that the oxidation of the methionine in the peptide P140 enhance the stability of the peptide. P140(MO) is stable at all the tested concentration over 100 days.

Example 2

Therapeutic Effect of the Peptides in MRL/Lpr Mice

MRL/lpr mouse strain is a mouse substrain that is genetically predisposed to the development of systemic lupus erythematosus-like syndrome, which has been found to be clinically similar to the human disease. It has been determined that this mouse strain carries a mutation in the fas gene. Also, the MRL/lpr is a useful model to study behavioural and cognitive deficits found in autoimmune diseases and the efficacy of immunosuppressive agents [Monneaux et al., 2003, Eur. J. Immunol. 33, 287-296].

2.1—Survival Analysis

Five-week-old female MRL/lpr mice received P140 or peptide P140(MO) intravenously as described (Monneaux et al., 2003, Eur. J. Immunol. 33, 287-296). All experimental protocols were carried out with the approval of the local Institutional Animal Care and Use Committee (CREMEAS). As control, mice were injected with NaCl.

Twenty mice were used for each peptide or NaCl.

Figure 2:
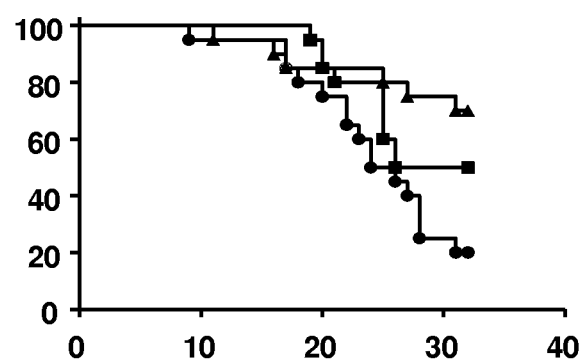
FIG. 2 is a Kaplan-Meier graph representing the cumulative survival rate (in percent) over the time (expressed in weeks) of mice injected with NaCl (line with circles), the peptide consisting of SEQ ID NO: 1, in which serine at position 10 is phosphorylated (line with squares) and compound II according to the invention (lines with triangles).

The results are shown in FIG. 2.

A Log-rank (Mantel-Cox) Test has been applied and the results are the following: NaCl vs P140 p=0.0686, NaCl vs P140(MO) p=0.0026, P140 vs P140 M(O) p=0.2366.

The Median survival of mice is: NaCl=25 weeks, P140=29 weeks and P140 (MO)>40 weeks. These results demonstrate the efficacy of the P140(MO) peptide in vivo in the treatment of lupus, in mice.

2.2—Proteinuria Analysis

Proteinuria of the above mice was measured in fresh urine using Albustix (Bayer Diagnostics) and was semi-quantitatively estimated according to a 0-4 scale recommended by the manufacturer (no proteinuria=0; traces=1; 1+=2; 2+=3; 3+=4; 4+=5).

Figure 3:
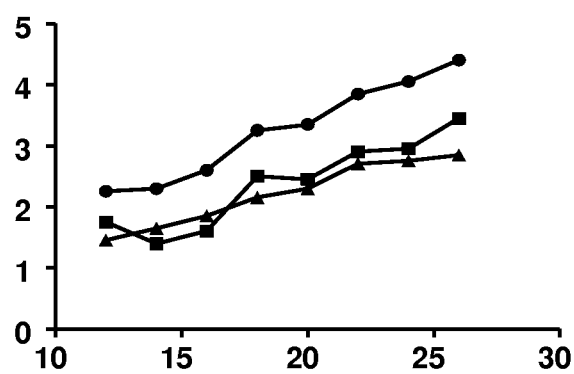
FIG. 3 represents the proteinuria score over the time (expressed in weeks) of mice injected with NaCl (line with circles), the peptide consisting of SEQ ID NO: 1, in which serine at position 10 is phosphorylated (line with squares) and compound II according to the invention (lines with triangles).

The results are shown in FIG. 3.

In this figure, it is observed that the proteinuria is less important and appears lately in P140 M(O)-treated mice compared to the untreated mice.

2.3—Cellularity Analysis

MRL/lpr mice were injected with 100 µg/100 µL of P140 or P140(MO) and cellularity (peripheral blood) was studied 5 days after this unique injection. The count includes all the leucocytes. In view of the low number of tested mice, a non parametric statistical test has been realised Mann-Whitney).

Figure 4:
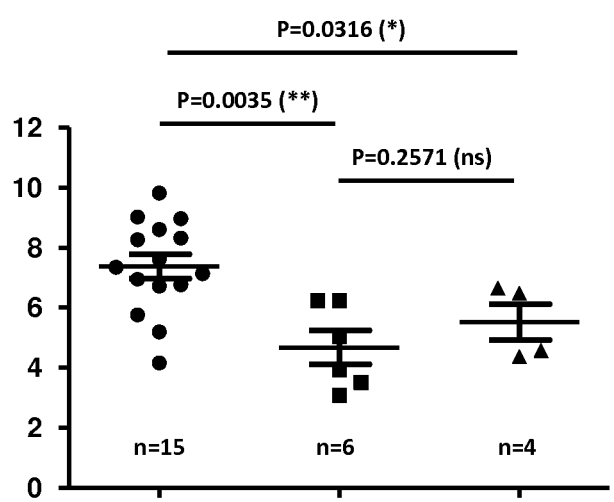
FIG. 4 represents the measure of the hypercellularity of MRL/lpr mice cells. Y-axis represents the number of cells/ mL of blood (×10⁶), in mice treated with NaCl (circles), the peptide consisting of SEQ ID NO: 1, in which serine at position 10 is phosphorylated (squares) and compound II according to the invention (triangles).

The Results are Shown in FIG. 4.

Thus, in an acute murine model of lupus, peptide of SEQ ID NO: 4 was able to decrease peripheral hypercellularity and delays biological and clinical signs of the disease with an efficacy at least similar to that of P140, or better.

Example 3

Affinity of the Peptides for HSC70 Protein

BIAcore 3000 system (Biacore AB) was used to evaluate the binding of P140 peptides to HSC70 protein (Page et al., 2009, and 2011). Sensor chip CMS, surfactant P20, amine coupling kit containing N-hydroxysuccinimide (NHS) and N-ethyl-N'-dimethylaminopropyl carbodiimide (EDC), 2-(2-pyridinyldithio)ethaneamine (PDEA) and ethanolamine were from Biacore AB. Biosensor assays were performed with HBS-EP buffer as running buffer (10 mM HEPES, 150 mM NaCl, 3 mM EDTA, 0.005% surfactant P20, pH 7.4). The compounds were diluted in the running buffer. The sensor chip surface was regenerated after each experiment by injecting 10 µL of 10 mM HCl. Recombinant bovine HSC70 (Stressgen) was immobilized on flow cells of a CMS sensor chip through its thiol groups using 35 µL PDEA in 50 mM borate buffer, pH 8.3 on the NHS/EDC-activated matrix. Then, 35 µL of HSC70 (100 µg/mL in formate buffer, pH 4.3) were injected until a response of 13,000 response units (RU) corresponding to 13 ng/mm² of HSC70 was immobilized. Twenty µL of a 50 mM cysteine/1 M NaCl solution was used to saturate unoccupied sites on the chip. The direct binding measurement of P140 peptides to HSC70 was carried out at 25° C. with a constant flow rate of 20 µL/min. P140 peptide and analogues were injected in the flux at different concentrations for 3 min, followed by a dissociation phase of 3 min. The kinetic parameters were calculated using the BIAeval 3.1 software on a personal computer. Analysis was performed using the simple 1:1 Langmuir binding model. The specific binding profiles were obtained after subtracting the response signal from the control empty channel and from blank-buffer injection. The fitting to each model was judged by the $\chi^2$ value and randomness of residue distribution compared to the theoretical model.

Figure 5:
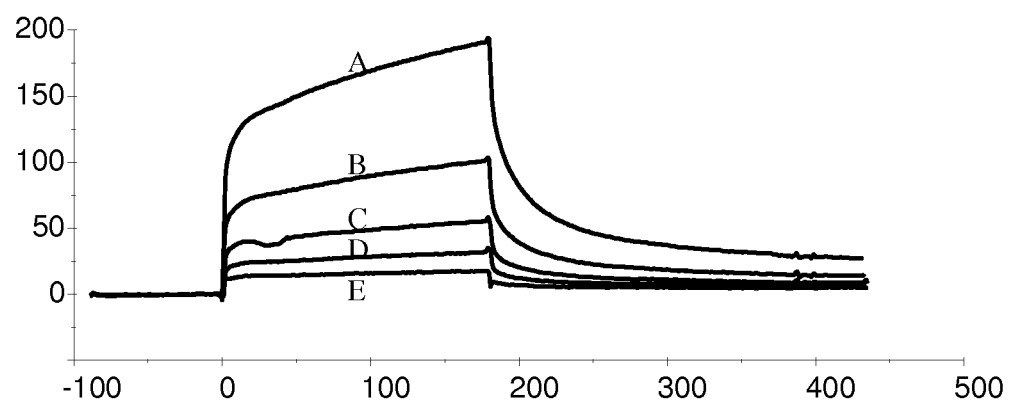
FIG. 5 represents the measure of the affinity for the HSC70 protein of the peptide consisting of SEQ ID NO: 1, in which serine at position 10 is phosphorylated. Curves corresponds to the Biacore response over the time (expressed in seconds) by using the peptide consisting of SEQ ID NO: 1, in which serine at position 10 is phosphorylated at a concentration of 25 µM(A), 12.5 µM(B), 6.25 µM(C), 3.12 µM(D) and 1.56 µM (E).
Figure 6:
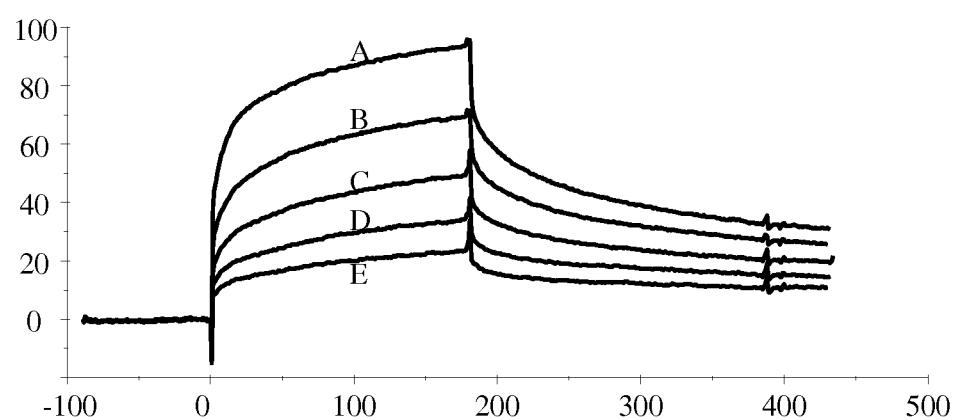
FIG. 6 represents the measure of the affinity of the compound II according to the invention, for the HSC70 protein. Curves correspond to the Biacore response over the time (expressed in seconds) by using the compound II at a concentration of 25 µM(A), 12.5 µM(B), 6.25 µM(C), 3.12 µM(D) and 1.56 µM (E).

Results are shown in the tables 3 and 4, and in FIGS. 5 and 6

These tables demonstrate that the affinity for HSC70 is not statistically different between P140 and P140 M(O) peptides.

Thus, these two peptides bind with the same efficiency HSC70.

TABLE 3

P140 on HSC70

| Peptide - concentration | ka (1/Ms) | kd (1/s) | Rmax (RU) | RI (RU) | Conc of analyte | KA (1/M) | KD (M) | Req (RU) | kobs (1/s) | Chi2 |
| --- | --- | --- | --- | --- | --- | --- | --- | --- | --- | --- |
|  | 450 |  | 83.3 |  |  |  |  |  |  | 3.17 |
| P140-1.56 µM |  | 3.12E−03 |  | 12.1 | 1.56 u | 1.44E+05 | 6.94E−6 | 15.3 | 3.82E−03 |  |
| P140-3.12 µM |  | 3.12E−03 |  | 20.9 | 3.12 u | 1.44E+05 | 6.94E−6 | 25.8 | 4.52E−03 |  |
| P140-6.25 µM |  | 3.12E−03 |  | 33.8 | 6.25 u | 1.44E+05 | 6.94E−6 | 39.5 | 5.93E−03 |  |
| P140-12.5 µM |  | 3.12E−03 |  | 62.5 | 12.5 u | 1.44E+05 | 6.94E−6 | 53.6 | 8.74E−03 |  |
| P140-25 µM |  | 3.12E−03 |  | 118 | 25 u | 1.44E+05 | 6.94E−6 | 65.2 | 0.0144 |  |

TABLE 4

P140(MO) on HSC70

| Peptide - concentration | ka (1/Ms) | kd (1/s) | Rmax (RU) | RI (RU) | Conc of analyte | KA (1/M) | KD (M) | Req (RU) | kobs (1/s) | Chi2 |
| --- | --- | --- | --- | --- | --- | --- | --- | --- | --- | --- |
|  | 1.15E+3 |  | 39 |  |  |  |  |  |  | 1.18 |
| P140(MO)-1.56 µM |  | 2.20E−3 |  | 14 | 1.56 u | 5.24E+5 | 1.91E−6 | 17.6 | 4.00E−03 |  |
| P140(MO)-3.12 µM |  | 2.20E−3 |  | 18.7 | 3.12 u | 5.24E+5 | 1.91E−6 | 24.2 | 5.80E−03 |  |
| P140(MO)-6.25 µM |  | 2.20E−3 |  | 25.9 | 6.25 u | 5.24E+5 | 1.91E−6 | 29.9 | 9.40E−03 |  |
| P140(MO)-12.5 µM |  | 2.20E−3 |  | 36.9 | 12.5 u | 5.24E+5 | 1.91E−6 | 33.9 | 0.0166 |  |
| P140(MO)-25 µM |  | 2.20E−3 |  | 53.4 | 25 u | 5.24E+5 | 1.91E−6 | 36.3 | 0.031 |  |

The invention claimed is:

1. A peptide, or a salt thereof, comprising or consisting of the amino acid sequence of SEQ ID NO: 2

[SEQ ID NO: 2]
IHMVYSKRSGKPRGYAFIEY, comprising a phosphoserine at position 9, and an oxidized Methionine at position 3.

2. A peptide, or salt thereof, comprising or consisting of the amino acid sequence of SEQ ID NO: 1

[SEQ ID NO: 1]
RIHMVYSKRSGKPRGYAFIEY, comprising a phosphoserine at position 10, and an oxidized Methionine at position 4.

3. A composition comprising a peptide according to claim 1 or 2, and a drug having an immunosuppressive or an immunomodulatory effect.

4. A pharmaceutical composition comprising a peptide according to claim 1 or 2, further comprising a pharmaceutically acceptable carrier.

5. The pharmaceutical composition according to claim 4, which is in the form of a lozenge, tablet, gelatin, capsule, drop, pill, liposome, nano particles or in the form of a solution.

6. A method of treating an autoimmune disease, wherein the method comprises the step of administering to a patient in need of such treatment a pharmaceutical composition according to claim 4, in an amount sufficient to effect said treatment.

7. The method according to claim 6, wherein said autoimmune disease is chosen among autoimmune pathologies of the family of connective tissue diseases (non-specific systemic organ diseases); and/or organ-specific autoimmune pathologies.

8. The method according to claim 6, wherein said autoimmune disease is SLE.

9. The method according to claim 6, wherein the peptide of said pharmaceutical composition is administered at a dosage in an amount in a range of about 100 ng to about 5 mg.

10. The method of claim 7, wherein the connective tissue diseases is systemic lupus erythematosus (SLE), rheumatoid arthritis, mixed connective tissue disease, Sjögren's syndrome, or chronic juvenile arthritis.

11. The method of claim 7, wherein the organ-specific autoimmune pathologies is multiple sclerosis, insulin-dependent diabetes, Crohn's disease, or bullous diseases.

* * * * *